United States Patent [19]

Osada et al.

[11] Patent Number: 4,569,592
[45] Date of Patent: Feb. 11, 1986

[54] PLASMA MONITOR

[75] Inventors: Hisajiro Osada, Tokyo; Yutaka Hiratsuka, Yokohama, both of Japan

[73] Assignee: Hitachi, Ltd., Tokyo, Japan

[21] Appl. No.: 445,093

[22] Filed: Nov. 29, 1982

[30] Foreign Application Priority Data

Dec. 11, 1981 [JP] Japan ................................ 56-198401

[51] Int. Cl.$^4$ ........................ G01J 3/443; G01N 21/64
[52] U.S. Cl. .................................... 356/318; 156/626; 250/458.1; 356/316
[58] Field of Search ................................ 356/316–318; 204/192 E; 250/458.1, 459.1, 461.1; 156/626

[56] References Cited

U.S. PATENT DOCUMENTS 4,394,237 7/1983 Donnelly et al. ................ 204/192 E

OTHER PUBLICATIONS

Donnelly et al., *J. Vac. Sci. Technol.*, vol. 21, No. 3, Sep./Oct. 1982, pp. 817–823.

*Primary Examiner*—F. L. Evans
*Attorney, Agent, or Firm*—Antonelli, Terry & Wands

[57] ABSTRACT

A plasma monitor which measures the distribution of particular chemical species (atom, molecule, ion) in plasma generated inside an instrument making use of the plasma. Laser light having a particular wavelength is radiated to the particular chemical species so as to let it generate fluorescence. The fluorescence is picked up for each of a plurality of zones divided in the radiating direction of the laser light and the construction of the chemical species in each zone is determined on the basis of the intensity of the fluorescence in each zone in order to determine the concentration distribution of the particular chemical species contained in the plasma. The operative condition within the sealed vessel can be grasped more accurately by measuring the distribution of the concentration of the chemical species which is closely related with the condition of deposition or etching.

2 Claims, 2 Drawing Figures

PLASMA MONITOR

BACKGROUND OF THE INVENTION

This invention relates to a plasma monitor for measuring the distribution of particular chemical species such as particular atoms, molecules, ions and the like contained in plasma generated inside an instrument making use of the plasma such as sputtering and dry-etching instruments.

Plasma monitors making use of the light emission of plasma generated inside an instrument have been proposed in the past so as to determine the film deposition rate or the film composition in sputtering or the etching rate or the end point of etching in dry-etching.

In plasma monitors for dry-etching, for example, the light emitted by the material to be etched is taken out from the plasma and the etching rate or the end point of etching is detected by the intensity (related to concentration of species) of the light.

In plasma monitors for sputtering, on the other hand, the light emission of two particular kinds of chemical species is taken out from the plasma generated during sputtering and the film deposition rate or the film composition is detected by the ratio of these chemical species.

In the conventional plasma monitors of the kinds described above, however, the light emission of the plasma generated inside the instruments is collected as a whole and hence, the plasma condition is grasped only in the gross.

In other words, the plasma monitors of the prior art fail to grasp the variance of the conditions of deposition or etching inside the instrument because they can not measure the distribution of the concentration of chemical species contained in the plasma generated inside the instrument. For this reason, data necessary for controlling suitably the conditions of etching or sputtering can not be obtained even though excessive or insufficient etching is likely to occur in the case of dry-etching or variance occurs in the thickness of the deposited film or in the film composition in the case of sputtering.

SUMMARY OF THE INVENTION

It is therefore an object of the present invention to provide a plasma monitor which can accurately measure the three-dimensional distribution of particular chemical species in the plasma generated in an instrument using the plasma.

It is another object of the present invention to provide a plasma monitor which can accurately measure the three-dimensional distribution of the particular chemical species in the plasma generated in the instrument and can accurately detect the conditions to deposit or sputter homogeneously.

To accomplish these objects, the present invention is characterized in that laser light having a particular wavelength is radiated to the plasma generated inside the instrument so as to excite the particular chemical species and to let it generate fluorescence, the ordinates of the measuring position inside the plasma are determined from the radiating position of the laser light and the receiving position of the fluorescence and the concentration of the chemical species at the position of the ordinate is determined from the intensity of the fluorescence thus received.

DESCRIPTION OF THE PREFERRED EMBODIMENTS

Figure 1:
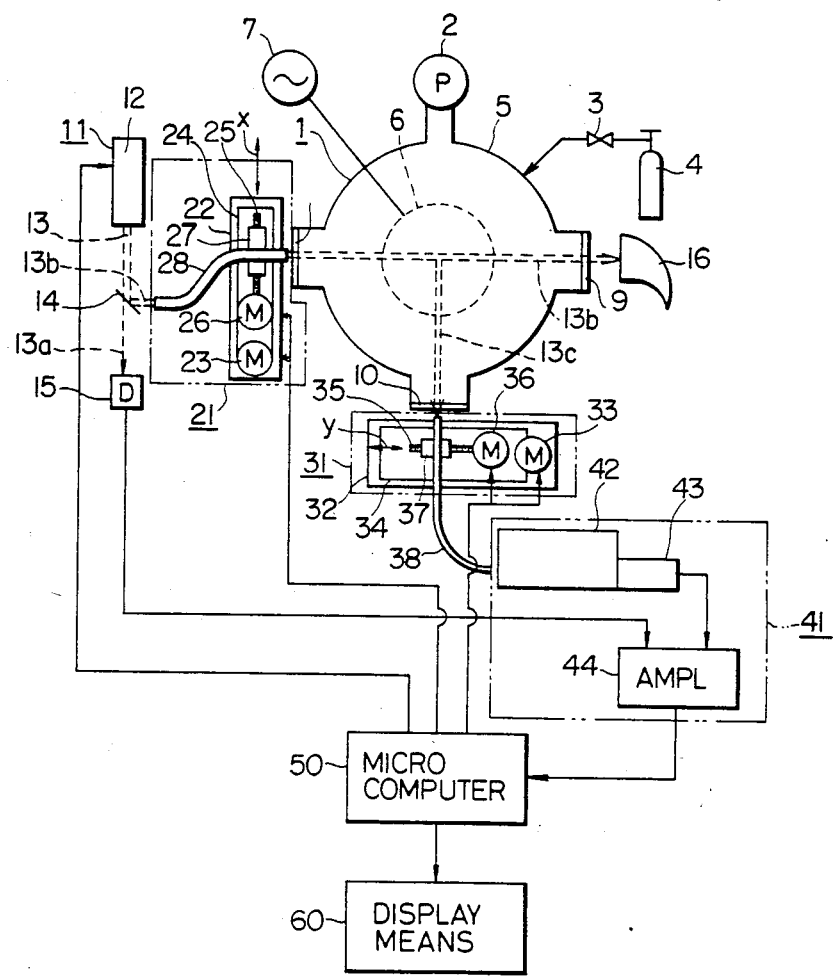
FIG. 1 is a schematic diagram showing the plasma monitor in accordance with one embodiment of the present invention.

FIG. 1 shows an example of the plasma monitor in accordance with the present invention.

The plasma monitor includes laser generation means 11 mounted to an instrument 1; scanning means 21 for guiding the laser light generated by the laser generation means 11 to a sealed vessel 5, moving the radiating position of the laser light and scanning the radiating positions of the laser light; light receiving means 31 for changing the light receiving position in response to scanning of the laser light so as to receive the fluorescence excited by the radiation of the laser light; detection means 41 for taking out the fluorescence among the light received by the light receiving means 31 and generating an electric signal in accordance with the fluorescent intensity; a micro-computer 50 for controlling the radiating position and light receiving position of the scanning means 21 and light receiving means 31, respectively, and calculating the concentration of the chemical species in accordance with the output of the detection means 41; and display means 60 for displaying the signal of the detection position impressed by the micro-computer 50 and the concentration of the chemical species at that position.

The instrument 1 consists of a vacuum pump 2, a sealed vessel 5 connected to a gas feed source 4 via a flow regulating valve 3, an electrode 6 disposed inside the sealed vessel 5 and a power source 7 for impressing a predetermined voltage upon this electrode 6. The sealed vessel 5 is equipped with a window 8 for introducing the laser light, a window 9 through which the laser light introduced into the sealed vessel 5 passes, and a window 10 for taking out the fluorescence generated by the chemical species that are excited by the laser light.

The laser generation means 11 consist of a laser generator 12 which generates the laser light on the basis of the instruction from the micro-computer 50, a splitter 14 which splits the laser light 13 generated by the laser generator 12 by a predetermined ratio, a trigger detector 15 which receives one of the laser light (13a) split by the splitter 14 and detects the generation of the laser light and a laser trap 16 which is disposed so as to face the aforementioned window 9 and receives the other of the laser light (13b) that passes through the vacuum vessel after being split by the splitter 14.

The scanning means 21 are disposed between the laser generation means 11 and the window 8 and consist of a fixed table 22, screw transmission means (not shown) consisting of a feed screw turnably supported by the fixed table 22 and a nut mating with this feed screw, a motor 23 for rotating the feed screw, a first moving table 24 coupled to the nut, slidably guided by a guide member (not shown) and moving in the direction perpendicular to the sheet of FIG. 1 of the drawings (hereinafter referred to as the "Z direction") by the operation of the motor 23, a feed screw 25 turnably supported by the moving table 24, a motor 26 for rotating this feed screw 25, a second moving table 27 connected to a nut (not shown) mating with the feed screw 25, slidably guided by a guide member (not shown) and moving in the X direction by the operation of the motor 26 and an optical fiber 28 whose one end is fixed so as to oppose the aforementioned splitter 14 and whose other end is fixed to the moving table 27 so as to oppose the window 8.

In the plasma monitor having the construction described above, the laser light 13b which is split by the splitter 14 and is incident to one end of the optical fiber 28 is guided by the optical fiber 28 and is radiated towards the window 8 from the end portion of the optical fiber 28 that opposes the window 8. The laser light 13b passes through the window 8, then through the inside of the sealed vessel 5, further through the window 9 and is thereafter caught by the laser trap 16.

When the motors 23 and 26 operate upon instruction of the micro-computer 50 in this instance, the moving table 27 moves inside the plane parallel to the window 8 so that the radiating position of the laser light 13b can be arbitrarily moved. In other words, the inside of the sealed vessel 5 can be scanned by the laser light 13b.

The light receiving means 31 are disposed along the window 9 of the sealed vessel 5 and consist of a fixed table 32, screw transmission means (not shown) consisting of a feed screw and a nut mating with this screw, a motor 33 for rotating the feed screw, a first moving table 34 coupled to the nut, slidably guided by a guide member (not shown) and moving in the Z direction by the operation of the motor, a feed screw 35 turnably supported by the moving table 34, a motor 36 for rotating the feed screw 35, a second moving table 37 connected to a nut (not shown) mating with the feed screw 35, slidably guided by a guide member (not shown) and moving in the Y direction by the operation of the motor 36 and an optical fiber 38 whose one end is fixed to the moving table 37 so as to oppose the aforementioned window 10 and whose other end is connected to the detection means 41.

According to the construction described above, the optical fiber 38 receives the fluorescence passing through the window 10 and guides it to the detection means 41. The fluorescence that can be received by the optical fiber 38 in this case is those which are embraced within the range of a truncated cone that is determined by the light receiving angle of the optical fiber 38. Accordingly, when the laser light 13b is radiated in such a manner as to cross transversely the range of the truncated cone, the optical fiber 38 can receive the fluorescence 13c generated by the chemical species that are excited by the laser light 13b. The intensity of the fluorescence 13c received by the optical fiber becomes maximum when the laser light 13b transversely crosses the center of the range of the truncated cone, and the micro-computer 50 gives the instruction to the motor 33 so that the optical fiber 38 moves in the Z direction in synchronism with the movement of the laser light in the Z direction. As to the Y direction, the micro-computer 50 gives the instruction to the motor 36 so that pitch feed in several divided pitches is effected in accordance with the light receiving angle of the optical fiber 38, for example.

The detection means 41 consist of a spectroscope 42 connected to one end of the optical fiber 38, a photo-electric convertor 43 connected to the spectroscope 42 and converting the fluorescence 13c taken out by the spectroscope 42 into an electric signal in accordance with the intensity of the fluorescence, and an amplifier 44 connected to the photo-electric convertor 43 and to the aforementioned trigger detector 15 and amplifying the output of the photo-electric convertor 43 only when a signal is applied from the trigger detector 15.

Figure 2:
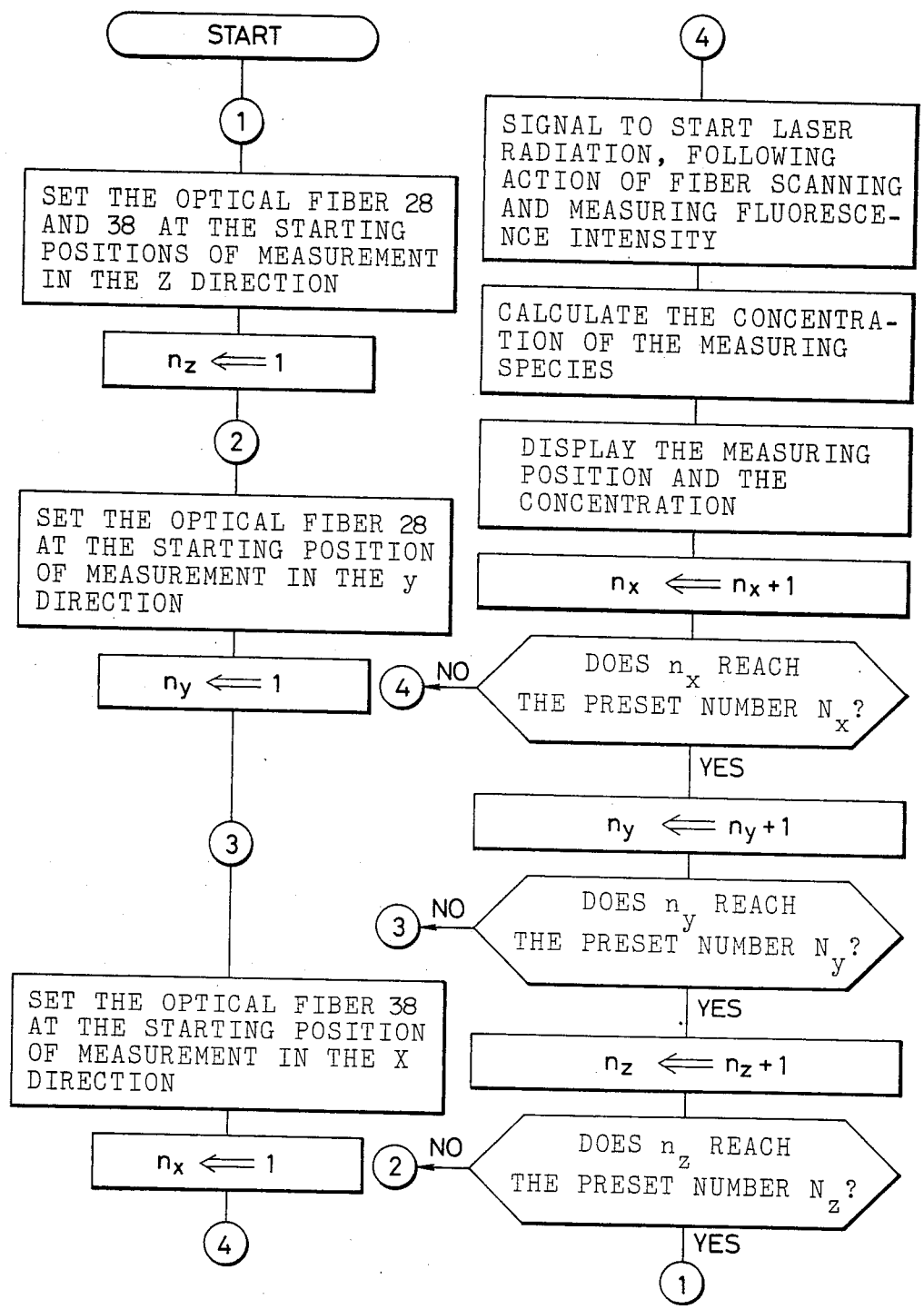
FIG. 2 is a flowchart of the program of the micro-computer.

The micro-computer 50 controls the laser generator 12 and each of the aforementioned motors 23, 26, 33 and 36 on the basis of the flowchart such as shown in FIG. 2 and calculates the concentration of the chemical species on the basis of the electric signal applied from the amplifier 44.

According to the construction described above, the micro-computer 50 calculates the light radiating position of the laser light 13c and the light receiving position of the fluorescence 13c from the instruction given to the motors 23, 26, 33, 36, determines the ordinates of the detection position inside the sealed vessel 5 and calculates the concentration of the chemical species at the ordinates.

The display means 60 display the ordinates of the detection position and the concentration of the chemical species that are calculated by the micro-computer 50, respectively.

In the plasma monitor having the construction described above, the wavelength of the laser light 13 generated by the laser generator 12 is set to the wavelength that excites the atom, molecule or ion to be monitored. If the aluminum (Al) atom is monitored, for example, the wavelength of the laser light 13 is set to 394.4 nm. It is likewise set to 490 nm for the chlorine molecule ($Cl_2$), and to 439.6 nm for the chlorine ion ($Cl_2^+$).

On the other hand, the end of the optical fiber 28 facing the window 8 and the end of the optical fiber 38 facing the window 10 are set to the measurement starting positions by the instruction from the micro-computer 50.

Under such a state, the laser light 13 having a wavelength of 394.4 nm, for example, is radiated from the laser generator 12 by the instruction of the micro-computer 50 for a short period of time (preferably below 0.1 sec). The laser light 13 is halved by the splitter 14 and one of the laser light (13a) is incident to the trigger detector 15 which detects the generation of the laser light 13. The other of the halved laser light is incident to the optical fiber 28, is guided by it to a predetermined position of the window 8, is then emitted from the optical fiber 28 through the window 5 and then through the sealed vessel 5, further through the window 9 and is thereafter caught by the light trap 16. If the chemical species such as the atoms, molecules, ions and the like exist in the path during the passage of the laser light 13b through the sealed vessel 5, the particular chemical species is excited in accordance with the wavelength of the laser light 13b and generates the fluorescence 13c. If the wavelength of the laser light 13b is 394.4 nm, the aluminum (Al) atom generates the fluorescence 13c having a wavelength of 396.15 nm. Similarly, the chlorine molecule ($Cl_2$) is excited and generates the fluorescence 13c having a wavelength of 505 nm when the wavelength of the laser light 13b is 490 nm.

This fluorescence 13c is received by the optical fiber 38 together with other plasma light through the window 10 and is guided to the spectroscope 42, which resolutes the spectra. The fluorescence 13c separated from other wavelength is incident to the photo-electric convertor 43 and is converted into a signal in accordance with the intensity of the fluorescence 13c. This signal is applied to the amplifier 44. In this case, since the signal is also applied to the amplifier 44 from the trigger detector 15, the amplifier 44 amplifies the signal applied from the photo-electric convertor 43 and applies the amplified signal to the micro-computer 50.

On the basis of the signal applied from the amplifier 44, the micro-computer 50 calculates the concentration of the particular chemical species in the plasma, determines the ordinates of the measuring position from the instruction it has given to the motors 23, 26, 33, 36 and applies these results to the display means 60.

The display means 60 display the measuring position and the concentration of the particular chemical species at that position on the basis of the instruction from the micro-computer 50.

After one pass of measurement is completed in the manner described above, the micro-computer 50 gives the instruction to the motor 36, for example, so that the moving table 34 is moved by one step (which is the unit zone divided by the light receiving angle of the optical fiber 38) for the second measurement.

These procedures are repeated a necessary number of times to accurately measure the distribution of the particular chemical species contained in the plasma.

It is obvious from the foregoing description that if the chemical species to be measured are suitably selected, the condition under operation can be grasped more accurately.

What is claimed is:

1. In a plasma monitor for measuring a particular chemical species inside a plasma generated in an instrument in order to grasp the operative condition inside said instrument making use of the plasma, the improvement comprising:

means for generating laser light having a wavelength exciting a chemical species to be measured and for moving the radiating positon of the laser light relative to the plasma so as to scan the plasma; and means for receiving fluorescence generated by the chemical species excited by the laser light, for determining the concentration of the chemical species on the basis of the intensity of the fluorescence, for determining a measuring position on the basis of the scanning position and a receiving position of the laser light and for displaying the measuring position as well as the concentration of the chemical species at that measuring position.

2. In a plasma monitor for measuring a particular chemical species inside a plasma generated in an instrument in order to grasp the operative condition inside said instrument making use of the plasma, the improvement comprising:

laser light generation means for generating laser light having a particular wavelength for exciting a particular chemical species contained in the plasma and for letting it generate fluorescence;

scanning means for moving the radiating position of the laser light generated by said laser light generation means relative to the plasma and thus scanning the plasma by the laser light;

light receiving means for receiving the plasma inside the light receiving angle thereof and the fluorescence generated by the chemical species excited by the laser light, and for changing the light receiving position;

detection means for taking out the fluorescence generated by the particular chemical species among the light received by said light receiving means and for converting it into an electric signal in accordance with the intensity of the fluorescence;

control means for calculating the ordinates of the detection position inside the plasma from an instruction signal given by said control means to said scanning means and to said light receiving means, and for calculating the concentration of the particular chemical species at the detection position on the basis of the electric signal applied thereto by said detection means; and display means for displaying the results of calculation applied thereto by said control means.

* * * * *